US008771724B2

(12) United States Patent
Ohtake et al.

(10) Patent No.: US 8,771,724 B2
(45) Date of Patent: Jul. 8, 2014

(54) PERCUTANEOUS ABSORPTION ENHANCER AND TRANSDERMAL PREPARATION USING THE SAME

(75) Inventors: Naoto Ohtake, Fukushima (JP); Yuuki Koide, Saitama (JP)

(73) Assignee: TOA EIYO Ltd., Tokyo (JP)

( * ) Notice: Subject to any disclaimer, the term of this patent is extended or adjusted under 35 U.S.C. 154(b) by 0 days.

(21) Appl. No.: 13/000,635

(22) PCT Filed: Jun. 22, 2009

(86) PCT No.: PCT/JP2009/002837
§ 371 (c)(1),
(2), (4) Date: Dec. 22, 2010

(87) PCT Pub. No.: WO2009/157173
PCT Pub. Date: Dec. 30, 2009

(65) Prior Publication Data
US 2011/0104241 A1 May 5, 2011

(30) Foreign Application Priority Data

Jun. 23, 2008 (JP) ................................. 2008-162730

(51) Int. Cl.
*A61K 9/70* (2006.01)
(52) U.S. Cl.
USPC ........................................................ 424/443
(58) Field of Classification Search
None
See application file for complete search history.

(56) References Cited

U.S. PATENT DOCUMENTS

| 5,958,447 | A | * | 9/1999 | Haralambopoulos et al. ............ 424/449 |
| 6,479,461 | B1 | | 11/2002 | Bousquet et al. |
| 7,052,714 | B1 | | 5/2006 | Tojo et al. |
| 2007/0259029 | A1 | | 11/2007 | McEntire et al. |
| 2008/0139392 | A1 | * | 6/2008 | Acosta-Zara et al. ......... 504/359 |
| 2008/0152604 | A1 | * | 6/2008 | Doering et al. ................. 424/60 |

FOREIGN PATENT DOCUMENTS

| JP | 63 218631 | | 9/1988 | |
| JP | S63218631 | * | 9/1988 | ............. A61K 47/00 |
| JP | 7 17851 | | 1/1995 | |
| JP | 10 182455 | | 7/1998 | |
| WO | 01 26648 | | 4/2001 | |
| WO | WO 2006/091722 A2 | | 8/2006 | |
| WO | WO 2006/091722 A3 | | 8/2006 | |
| WO | 2007 126067 | | 11/2007 | |

OTHER PUBLICATIONS

Anderberg et al., Epithelial Transport of Drugs in Cell Culture. VII: Effects of Pharmaceutical Surfactant Excipients and Bile Acids on Transepithelial Permeability in Monolayers of Human Intestinal Epithelial (Coco-2) cells, Dec. 5, 1991, Journal of Pharmaceutical Sciences, vol. 81. No. 9, Sep. 1992.*
Narasimha, S., et al., "n-Octyl-β-thioglucoside enhances the transdermal permeation of ketotifen," Pharmazie, vol. 61, pp. 75-76, (2006).
International Search Report issued Aug. 18, 2009 in PCT/JP09/002837 filed Jun. 22, 2009.
M. Trotta, et al., "Influence of counter ions on the skin permeation of methotrexate from water-oil microemulsions", Pharmaceutica Acta Helvetiae, vol. 71, XP055085646, Jan. 1, 1996, pp. 135-140.
Taro Ogiso, et al., "Mechanism of the Enhancement Effect of n-Octyl-Beta-D-thioglucoside on the Transdermal Penetration of Fluorescein Isothiocyanate-Labeled Dextrans and the Molecular Weight Dependence of Water-Soluble Penetrants through Stripped Skin", Journal of Pharmaceutical Sciences, vol. 83, No. 12, XP055085720, Dec. 1994, pp. 1676-1681.
Adrian C. Williams, et al., "Penetration enhancers", Advanced Drug Delivery Reviews, vol. 56, No. 5, Elsevier, XP002463042, Mar. 27, 2004, pp. 603-618.
Extended European Search Report issued Nov. 7, 2013 in European Patent Application No. 09769883.1.

* cited by examiner

*Primary Examiner* — Anand Desai
*Assistant Examiner* — Melissa Mercier
(74) *Attorney, Agent, or Firm* — Oblon, Spivak, McClelland, Maier & Neustadt, L.L.P.

(57) ABSTRACT

Provided are a percutaneous absorption enhancer excellent in an enhancing effect on percutaneous absorption of a wide range of drugs and excellent in compatibility with an adhesive base, and a transdermal preparation using the percutaneous absorption enhancer. The percutaneous absorption enhancer includes a sulfosuccinate or a salt thereof and an alkyl glycoside or an alkyl thioglycoside.

14 Claims, No Drawings

PERCUTANEOUS ABSORPTION ENHANCER AND TRANSDERMAL PREPARATION USING THE SAME

CROSS-REFERENCE TO RELATED APPLICATIONS

This application is a National Stage of PCT/JP09/002837 filed Jun. 22, 2009 and claims the benefit of JP 2008-162730 filed Jun. 23, 2008.

FIELD OF THE INVENTION

The present invention relates to a practical percutaneous absorption enhancer that enhances percutaneous absorption of various kinds of drugs and does not adversely affect production of a preparation.

BACKGROUND OF THE INVENTION

An oral administration using a tablet, a capsule, a syrup, or the like has been performed as a method of administration of a drug for various kinds of medicaments. However, the oral administration has included drawbacks such as insufficient sustainability of a drug effect and the fact that a concentration of a drug in blood is temporarily increased to an excessive level after the administration, and hence an adverse side effect is likely to occur. In order to eliminate such drawbacks involved in the oral administration, development of a transdermal preparation, particularly, a tape preparation in which an adhesive matrix layer containing a drug is provided on one surface of a support such as a plastic film has been carried out. The tape preparation is expected not only to compensate those drawbacks but also to exhibit advantages such as decreasing the number of administration, improving compliance, ease of administration, and ease of stopping the administration. Further, the tape preparation is known to be more useful for elderly patients and child patients. Moreover, the tape preparation sustains a preparation function even after cutting unlike a reservoir-type preparation, and hence adjusting the dose of administration (area) depending on the age and body size of a patient is easy.

However, most drugs generally have low skin permeability, and hence the development of a transdermal preparation is difficult. The structure of skin is mainly formed of epidermis, dermis, and subcutaneous tissue. The outermost side of epidermis is covered with dead and keratinized cells having a thickness of 10 to 15 μm called a stratum corneum. The stratum corneum functions as a preventive barrier against the inflow and outflow of chemicals including drugs and water evaporation. That is, the rate-limiting step of percutaneous absorption lies in a process of permeating a corneum, and hence, in the case of the development of a tape preparation, enhancing the drug permeability into the stratum corneum has been the most important issue.

Thus, in order that the barrier function of the stratum corneum may be weakened in order for the stratum corneum to absorb a sufficient amount of drugs, studies on percutaneous absorption enhancers have been widely carried out. Examples of the percutaneous absorption enhancers include: fatty acids, fatty alcohols, fatty acid esters, fatty acid amides, and fatty acid ethers each having 6 to 20 carbon chains; aromatic organic acids, aromatic alcohols, aromatic organic acid esters, and aromatic organic acid ethers; and further, lactates, acetates, monoterpene-based compounds, sesquiterpene-based compounds, azone, azone derivatives, pyrrothiodecane, glycerol fatty acid esters, propylene glycol fatty acid esters, sorbitan fatty acid esters, polyethylene glycol fatty acid esters, polyoxyethylene hardened castor oils, polyoxyethylene alkyl ethers, sucrose fatty acid esters, and vegetable oils. Further, surfactants such as alkyl glycosides are also known to be used as percutaneous absorption enhancers (see, for example, Patent Literature 1 and Non Patent Literature 1).

On the other hand, in order to obtain a tape preparation, in addition to the percutaneous absorbability of drugs, providing a good balance among requirements such as (1) drugs are released well from an adhesive layer, (2) drugs are transferred into skin for a long time, (3) adhesiveness to the surface of skin is preferable, (4) neither a residual glue on the surface of skin nor cobwebbing occurs at the time of detachment, and (5) irritation to skin is slight, should be necessary. Thus, in the case of the development of the tape preparation, it has been conventionally necessary to study, for example, the chemical properties and physical properties of a target drug, an adhesive base, a percutaneous absorption enhancer, and other components, and interactions caused by a combination of the target drug with other substances. As a result, only particularly limited drugs such as isosorbide dinitrate, nitroglycerin, scopolamine, estradiol, and tulobuterol have been put to practical use for the purpose of systemic administration.

In order to obtain a matrix-type preparation, the percutaneous absorption enhancer should not only exhibit a sufficient percutaneous absorption enhancing action to a drug, but also have excellent compatibilities with an adhesive base and other additives and not affect the agglomerating property, and adhesiveness to the surface of skin, of an adhesive layer. However, until now, there has been no percutaneous absorption enhancer obtained by studying various drugs and various adhesive bases from the above-mentioned viewpoint. There has been therefore demanded a practical percutaneous absorption enhancer that enhances percutaneous absorption of a wide range of drugs, is excellent in compatibility with various adhesive bases, and does not affect the agglomerating property, and adhesiveness to the surface of skin, of an adhesive layer.

PATENT DOCUMENTS

[Patent Document 1] US 2007/259029 A1

NON PATENT DOCUMENTS

[Non Patent Document 1] Pharmazie, Germany, Govi-Verlag Pharmazautischer Verlag, 2006, vol. 61, Ver 1, p 75-76

SUMMARY OF THE INVENTION

Problems to be Solved by the Invention

An object of the present invention is to provide a percutaneous absorption enhancer, which is excellent for an enhancing effect of percutaneous absorption of various kinds of drugs and excellent for compatibility with an adhesive base, and a transdermal preparation using the percutaneous absorption enhancer.

Means for Solving the Problem

The inventors of the subject invention have intensively studied the percutaneous absorbability of drugs. As a result, the inventors have found that an enhancing effect for percutaneous absorption of drugs can be remarkably increased by combining a sulfosuccinate or a salt thereof and an alkyl glycoside or an alkyl thioglycoside, compared with that in the case where each of these substances is used alone. Then, further studies have been made on those substances. As a result, the inventors have found that the resultant product is a percutaneous absorption enhancer which is excellent in practical application for production of a preparation because the resultant product has low irritation property to skin and is excellent in compatibility with various adhesive bases that are usually used in transdermal preparations. Thus, the inventors have completed the present invention.

Thus, the present invention provides a percutaneous absorption enhancer, including a sulfosuccinate or a salt thereof and an alkyl glycoside or an alkyl thioglycoside.

Further, the present invention provides a matrix-type transdermal preparation, containing the above-mentioned percutaneous absorption enhancer and a drug.

Further, the present invention provides a use of a combination of a sulfosuccinate or a salt thereof and an alkyl glycoside or an alkyl thioglycoside as a percutaneous absorption enhancer.

Further, the present invention is characterized in providing a method for enhancing percutaneous absorption of a drug, the method including transdermally administering the drug, a sulfosuccinate or a salt thereof, and an alkyl glycoside or an alkyl thioglycoside.

Effects of the Invention

According to the present invention, there can be provided a percutaneous absorption enhancer which has a high enhancing effect for percutaneous absorption by combining a sulfosuccinate or a salt thereof and an alkyl glycoside or an alkyl thioglycoside; and is excellent in practical application for production of a preparation because of its low irritation property to skin and excellent compatibility with various adhesive bases that are usually used in transdermal preparations.

The percutaneous absorption enhancer of the present invention enhances the percutaneous absorbability of a wide range of drugs. More preferably, the percutaneous absorption enhancer is blended in a tape preparation with a drug that is a compound having a carboxyl group or a bioisoster thereof and an aliphatic amino group and/or an aromatic amino group. As a result, the percutaneous absorbability of the drug is significantly improved, and hence intrinsic actions and effects of the drug can be sufficiently provided.

DETAILED DESCRIPTION OF THE INVENTION

A percutaneous absorption enhancer of the present invention is obtained by combining a sulfosuccinate or a salt thereof and an alkyl glycoside or an alkyl thioglycoside. The combination leads to a significant improvement in the percutaneous absorbability of drugs, compared with the case where each of those substances is used alone.

The sulfosuccinate or the salt thereof includes compounds which are used as anionic surfactants. The alkyl group or the alkanoyl group of each of those sulfosuccinates has preferably 6 to 18, and more preferably 6 to 14 carbon atoms. Examples of such surfactants include: alkyl ether sulfosuccinates such as disodium lauryl polyoxyethylene sulfosuccinate; alkyl sulfosuccinates such as disodium lauryl sulfosuccinate; dialkyl sulfosuccinates such as dioctyl sodium sulfosuccinate, bis(tridecyl) sodium sulfosuccinate, dihexyl sodium sulfosuccinate, dicyclohexyl sodium sulfosuccinate, diamyl sodium sulfosuccinate, and diisobutyl sodium sulfosuccinate; and alkylamide sulfosuccinates such as disodium polyoxyethylene lauroylethanolamide sulfosuccinate. Of those, sulfosuccinates or salts thereof, a $C_6$-$C_{18}$ dialkyl sulfosuccinate or a salt thereof is preferred, and dioctyl sodium sulfosuccinate is more preferred. As dioctyl sodium sulfosuccinate, dioctyl sodium sulfosuccinate, conforming to The Japanese Pharmaceutical Codex, can be used.

The alkyl glycoside or the alkyl thioglycoside includes compounds which are used as nonionic surfactants, and a $C_6$-$C_{18}$ alkyl glycoside or a $C_6$-$C_{18}$ alkyl thioglycoside is preferred. Examples of such surfactants include: heptyl-β-D-glucopyranoside, n-heptyl-β-D-thioglucopyranoside, n-octyl-α-D-glucopyranoside, n-octyl-β-D-glucopyranoside, n-octyl-β-D-thioglucopyranoside, n-octyl-β-D-maltopyranoside, n-nonyl-β-D-thiomaltopyranoside, n-nonyl-β-D-thioglucopyranoside, n-decyl-β-D-maltopyranoside, n-decyl-β-D-thiomaltopyranoside, n-dodecyl-β-D-glucopyranoside, n-dodecyl-α-D-maltopyranoside, n-dodecyl-β-D-maltopyranoside, and n-dodecyl-β-D-thiomaltopyranoside. Of those, n-octyl-β-D-thioglucopyranoside, n-dodecyl-β-D-glucopyranoside, or the like is preferred.

In the percutaneous absorption enhancer of the present invention, the blending ratio of a sulfosuccinate or a salt thereof to an alkyl thioglycoside may be appropriately selected. The blending ratio is, in terms of a weight ratio, preferably 1:0.1 to 1:10.0, more preferably 1:0.1 to 1:5.0, or even more preferably 1:0.1 to 1:2.0.

In the percutaneous absorption enhancer of the present invention, an additional percutaneous absorption enhancer may be contained. As a percutaneous absorption enhancer, any one of the compounds, which the absorption enhancing action into the skin is well-known, may be used. Examples of such compounds include: fatty acids such as caprylic acid, capric acid, caproic acid, lauric acid, myristic acid, palmitic acid, stearic acid, isostearic acid, oleic acid, linoleic acid, and linolenic acid; higher alcohols such as lauryl alcohol, myristyl alcohol, oleyl alcohol, isostearyl alcohol, and cetyl alcohol; esters such as methyl laurate, hexyl laurate, diethyl sebacate, lauric diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethylacetate, and propylacetate; terpenes such as geraniol, thymol, eugenol, terpineol, l-menthol, borneol, d-limonene, isoeugenol, isoborneol, nerol, and dl-camphor; and glycerol monocaprylate, glycerol monocaprate, glycerol monolaurate, glycerol monooleate, sorbitan monolaurate, sucrose monolaurate, polysorbate 20, propylene glycol, propylene glycol monolaurate, diethylene glycol monoethyl ether, polyethylene glycol monolaurate, polyethylene glycol monostearate, polyoxyethylene lauryl ether, HCO-60, pyrrothiodecane, and olive oil.

The percutaneous absorption enhancer of the present invention enhances percutaneous absorption of drugs in various transdermal preparations. Examples of such transdermal preparations include a tape preparation, a patch preparation, a cataplasm preparation, an ointment, and a cream preparation. A matrix-type transdermal preparation is more preferred. The tape preparation, in particular, a matrix-type tape preparation, is even more preferred, because the percutaneous absorption enhancer of the present invention is excellent in compatibility with an adhesive base and the matrix-type tape preparation containing the percutaneous absorption enhancer of the present invention is excellent in the agglomerating property, and adhesiveness to skin, of an adhesive layer.

In the transdermal preparation of the present invention, a sulfosuccinate or a salt thereof is used in the concentration range of preferably 0.01 to 10.0% by weight, more preferably 0.01 to 5.0% by weight, or even more preferably 0.01 to 2.5% by weight.

In the transdermal preparation of the present invention, an alkyl glycoside or an alkyl thioglycoside (hereinafter, may also be referred to as alkyl glycosides) is used in the concentration range of preferably 0.01 to 10.0% by weight, more preferably 0.01 to 5.0% by weight, or even more preferably 0.01 to 2.5% by weight.

The total amount of a sulfosuccinate or a salt thereof and alkyl glycosides may be preferably 0.1 to 20% by weight, more preferably 0.1 to 10% by weight, or even more preferably 0.1 to 5.0% by weight.

Drugs used in the transdermal preparation of the present invention are not particularly limited. Preferably used are pharmaceutical compounds that can be used by transdermal administration and are expected to exert systemic or local actions. Examples of the pharmaceutical compounds include nonsteroidal anti-inflammatory drugs, steroidal anti-inflammatory drugs, adrenergic receptor agonists, α-adrenergic receptor antagonists, β-adrenergic receptor antagonists, calcium antagonists, angiotensin-converting enzyme inhibitors, angiotensin II receptor blockers, antiarrhythmic drugs, diuretic drugs, antilipemic agents, peripheral vasodilators, cardiotonic agents, antianginal drugs, coronary vasodilators, anticoagulant drugs, psychotropic drugs, hypnotics, anesthetic drugs, antiemetic drugs, oral hypoglycemic drugs, hormone drugs, Parkinson's disease drugs, erectile dysfunction drugs, antihistamine drugs, bone resorption inhibitors, antineoplastics, antibiotics such as cephalosporin antibiotics and fluoroquinolone antibiotics, and vitamins.

Examples of the above-mentioned nonsteroidal anti-inflammatory drugs include salicylic acid, aspirin, sulpyrine hydrate, acetaminophen, diclofenac sodium, fenbufen, ibuprofen, aminoprofen, loxoprofen sodium hydrate, naproxen, oxaprofen, ketoprofen, tiaprofenic acid, sulindac, flufenamic acid aluminum, felbinac, mefenamic acid, indometacin, indometacin farnesil, acemetacin, proglumetacin maleate, bendazac, piroxicam, ampiroxicam, lornoxicam, tenoxicam, meloxicam, flurbiprofen, etodolac, tiaramide hydrochloride, and bucolome.

Examples of the above-mentioned steroidal anti-inflammatory drugs include hydrocortisone butyrate, prednisolone valerate acetate, methylprednisolone, hydrocortisone acetate, fluocinolone acetonide, triamcinolone acetonide, dexamethasone, betamethasone valerate, diflucortolone valerate, clobetasol propionate, and fluocinonide.

Examples of the above-mentioned adrenergic receptor agonists include epinephrine, norepinephrine, dopamine hydrochloride, phenylephrine hydrochloride, etilefrine hydrochloride, ephedrine hydrochloride, methylephedrine hydrochloride, clonidine hydrochloride, methyldopa, guanabenz acetate, guanfacine hydrochloride, isoprenaline hydrochloride, methoxyphenamine hydrochloride, orciprenaline sulfate, clorprenaline hydrochloride, trimetoquinol hydrochloride, salbutamol sulfate, terbutaline sulfate, hexoprenaline sulfate, tulobuterol hydrochloride, fenoterol hydrobromide, procaterol hydrochloride, clenbuterol hydrochloride, mabuterol hydrochloride, isoxsuprine hydrochloride, methamphetamine hydrochloride, methylphenidate hydrochloride, pemoline, imipramine hydrochloride, and amezinium metilsulfate.

Examples of the above-mentioned α-adrenergic receptor antagonists include urapidil, terazosin hydrochloride, bunazosin hydrochloride, prazosin hydrochloride, and doxazocin mesylate.

Examples of the above-mentioned-adrenergic receptor antagonists include bisoprolol fumarate, propranolol hydrochloride, tilisolol hydrochloride, bufetolol hydrochloride, bupranolol hydrochloride, atenolol, indenolol hydrochloride, alprenolol hydrochloride, oxprenolol hydrochloride, carteolol hydrochloride, nadolol, pindolol, timolol maleate, nipradilol, bunitrolol hydrochloride, penbutolol sulfate, bopindolol malonate, metoprolol tartrate, betaxolol hydrochloride, bevantolol hydrochloride, and acebutolol hydrochloride.

Examples of the above-mentioned calcium antagonists include verapamil hydrochloride, diltiazem hydrochloride, bepridil hydrochloride, clentiazem, nifedipine, nicardipine hydrochloride, felodipine, nisoldipine, cilnidipine, aranidipine, benidipine hydrochloride, manidipine hydrochloride, nilvadipine, nitrendipine, barnidipine hydrochloride, and efonidipine hydrochloride.

Examples of the above-mentioned angiotensin-converting enzyme inhibitors include alacepril, captopril, delapril hydrochloride, quinapril hydrochloride, benazepril hydrochloride, cilazapril hydrate, enalapril maleate, trandolapril, imidapril hydrochloride, lisinopril hydrate, perindopril erbumine, temocapril hydrochloride, and ramipril.

Examples of the above-mentioned angiotensin II receptor blockers include losartan potassium, candesartan cilexetil, valsartan, telmisartan, olmesartan medoxomil, and irbesartan.

Examples of the above-mentioned antiarrhythmic drugs include quinidine sulfate hydrate, ajmaline, procainamide hydrochloride, disopyramide, pirmenol hydrochloride, cibenzoline succinate, mexiletine hydrochloride, propafenone hydrochloride, pilsicainide hydrochloride, sotalol hydrochloride, and amiodarone hydrochloride.

Examples of the above-mentioned diuretic drugs include benzylhydrochlorothiazide, trichloromethiazide, methylclothiazide, ethacrynic acid, indapamide, chlorthalidone, tripamide, meticrane, mefruside, piretanide, furosemide, bumetanide, torasemide, azosemide, potassium canrenoate, spironolactone, triamterene, and acetazolamide.

Examples of the above-mentioned antilipemic agents include pravastatin sodium, simvastatin, fluvastatin sodium, atorvastatin calcium, rosuvastatin calcium, pitavastatin calcium, aluminium clofibrate, clinofibrate, bezafibrate, fenofibrate, nicomol, niceritrol, probucol, and ezetimibe.

Examples of the above-mentioned peripheral vasodilators include hydralazine hydrochloride, todralazine hydrochloride hydrate, budralazine, cadralazine, sodium nitroprusside, and isoxsuprine hydrochloride.

Examples of the above-mentioned cardiotonic agents include digitoxin, digoxin, methyldigoxin, lanatoside C, proscillaridin, dobutamine hydrochloride, docarpamine, denopamine, aminophylline hydrate, milrinone, vesnarinone, pimobendan, and ubidecarenone.

Examples of the above-mentioned antianginal drugs include amyl nitrite, nitroglycerin, isosorbide dinitrate, dilazep hydrochloride, and dipyridamole.

Examples of the above-mentioned coronary vasodilators include etafenone hydrochloride, trimetazidine hydrochloride, trapidil, and nicorandil.

Examples of the above-mentioned anticoagulant drugs include warfarin potassium, heparin sodium, and argatroban monohydrate.

Examples of the above-mentioned psychotropic drugs include chlorpromazine hydrochloride, perazine maleate, levomepromazine maleate, trifluoperazine hydrochloride, proclorperazine maleate, perphenazine, fluphenazine maleate, thioridazine hydrochloride, tiotixene, carpipramine hydrochloride, clocapramine hydrochloride hydrate, mosapramine hydrochloride, zotepine, haloperidol, spiperone, timiperone, bromperidol, pimozide, oxypertine, sulpiride, sultopride hydrochloride, tiapride hydrochloride, nemonapride, perospirone hydrochloride, quetiapine fumarate, risperidone, olanzapine, propericiazine, clotiazepam, etizolam, alprazolam, lorazepam, bromazepam, chlordiazepoxide, diazepam, oxazolam, cloxazolam, fludiazepam, mexazolam, ethyl loflazepate, imipramine hydrochloride, clomipramine hydrochloride, amitriptyline hydrochloride, nortriptyline hydrochloride, lofepramine hydrochloride, amoxapine, dosulepin hydrochloride, maprotiline hydrochloride, mianserin hydrochloride, setiptiline maleate, fluvoxamine maleate, paroxetine hydrochloride hydrate, milnacipran hydrochloride, trazodone hydrochloride, and lithium carbonate.

Examples of the above-mentioned hypnotics include flurazepam, haloxazolam, quazepam, nitrazepam, flunitrazepam, estazolam, nimetazepam, lormetazepam, rilmazafone hydrochloride, triazolam, midazolam, zopiclone, zolpidem tartrate, brotizolam, barbital, and amobarbital.

Examples of the above-mentioned anesthetic drugs include benzocaine, procaine hydrochloride, lidocaine hydrochloride, tetracaine hydrochloride, chloroprocaine, mepivacaine hydrochloride, dibucaine hydrochloride, bupivacaine hydrochloride, droperidol, and fentanyl citrate.

Examples of the above-mentioned antiemetic drugs include granisetron hydrochloride, azasetron hydrochloride, ondansetron hydrochloride, ramosetron hydrochloride, and tropisetron hydrochloride.

Examples of the above-mentioned oral hypoglycemic drugs include glibenclamide, gliclazide, glimepiride, repaglinide, nateglinide, mitiglinide calcium hydrate, metformin hydrochloride, buformin hydrochloride, voglibose, acarbose, miglitol, pioglitazone hydrochloride, and troglitazone.

Examples of the above-mentioned hormone drugs include: steroid hormones such as estrogen, estradiol, testosterone, and progesterone; peptide hormones such as insulin; and prostaglandin.

Examples of the above-mentioned Parkinson's disease drugs include trihexyphenidyl hydrochloride, profenamine hydrochloride, piroheptine hydrochloride, mazaticol hydrochloride, metixene hydrochloride, biperiden hydrochloride, amantadine hydrochloride, levodopa, carbidopa, benserazide, droxidopa, bromocriptine mesylate, talipexole hydrochloride, cabergoline, pergolide mesylate, and selegiline hydrochloride.

Examples of the above-mentioned erectile dysfunction drugs include sildenafil citrate, vardenafil hydrochloride, and tadalafil.

Examples of the above-mentioned vitamins include vitamin A, vitamin D, vitamin E, and vitamin K.

By the percutaneous absorption enhancer of the present invention, the release property of each of the various drugs as exemplified above from the transdermal preparation and the transitivity of each of the various drugs from skin into the body can be remarkably improved. In particular, the drugs are preferably components each having a relatively low molecular weight such as a molecular weight of 50 to 1000, and more preferably components each having a molecular weight of about 50 to 600. In particular, the drugs are preferably compounds each having a carboxyl group or a bioisoster thereof and an aliphatic amino group and/or an aromatic amino group. Here, examples of the bioisoster of the carboxyl group include groups such as an n-hydroxycarboxamide, an acylcyanamide, tetrazole, mercaptizol, sulfinylazole, sulfonylazole, isoxazole, isothiazole, hydroxythiadiazole, hydroxy-γ-pyrone, a phosphinate, a phosphonate, a phosphonamide, a sulfonate, a sulfonamide and an acylsulfonamide. Of those, an n-hydroxycarboxamide, tetrazole, a phosphinate, phosphonate, and a sulfonate are preferred.

As the above-mentioned compound having a carboxyl group or a bioisoster thereof and an aliphatic amino group and/or an aromatic amino group, there are exemplified delapril hydrochloride, ramipril, quinapril hydrochloride, benazepril hydrochloride, cilazapril hydrate, enalapril maleate, trandolapril, imidapril hydrochloride, temocapril hydrochloride, lisinopril hydrate, perindopril erbumine, irbesartan, candesartan cilexetil, valsartan, telmisartan, olmesartan medoxomil, atorvastatin calcium, pitavastatin calcium, rosuvastatin calcium, fluvastatin sodium, repaglinide, argatroban monohydrate, furosemide, piretanide, bumetanide, torasemide, fludarabine phosphate, tiagabine, etodolac, mofezolac, oxaprozin, tolmetin, diclofenac sodium, pranoprofen, ramatroban, ozagrel sodium, ozagrel hydrochloride, carumonam, tazobactam, panipenem, doripenem, meropenem, deferasirox, zanamivir hydrate, livostin, olopatadine hydrochloride, cetirizine hydrochloride, fexofenadine hydrochloride, betotastine besylate, clorazepate dipotassium, folic acid, pemetrexed disodium, calcium folinate, calcium levofolinate, methotrexate, cefoselis sulfate, cefdinir, ceftibuten, cefpirome, cefepime, cefixime, cefinenoxime hydrochloride, cefotiam hydrochloride, ceftriaxone sodium, cefozopran hydrochloride, ceftazidime, cefazolin sodium, ceftizoxime sodium, raltitrexed, tosufloxacin, sparfloxacin, prulifloxacin, nadifloxacin, gatifloxacin, fleroxacin, levofloxacin, gemifloxacin mesilate, enoxacin, norfloxacin, moxifloxacin hydrochloride, ofloxacin, lomefloxacin hydrochloride, carbidopa, ibandronate sodium, zoledronic acid monohydrate, risedronate, amlexanox, nedocromil sodium, lobenzarit disodium, montelukast, incadronate disodium, fosfluconazole, amfenac sodium, bromfenac sodium, 5-aminosalicylic acid, fudosteine, gabapentin, cefminox sodium, cefaclor, pazufloxacin mesilate, droxidopa, levodopa, alendronate sodium, pamidronate disodium, tranexamic acid, aspoxicillin, ampicillin sodium, amoxicillin, ubenimex, and baclofen.

The addition amount of any of the above-mentioned drugs may be appropriately determined depending on the kind of drugs and the purpose of drug use. In view of the effects of the present invention, when a transdermal preparation contains a drug at usually 0.1 to 30% by weight, preferably 0.1 to 10% by weight, or even more preferably 0.1 to 5% by weight, the percutaneous absorbability of the drug is improved, and hence the action and effect of the drug can be highly exerted.

Further, when the drug is contained in an amount exceeding 30% by weight, an increase in a pharmacological effect caused by an increase in the amount is not found, and moreover, adhesiveness to skin becomes inferior. Note that, from the viewpoints, for example, of imparting sustained-release property over a long time, of increasing a release amount of the drug by increasing its content per unit area, and of reducing the size of a preparation, the drug may be blended at a ratio equal to or more than the saturated solubility of the drug with respect to an adhesive layer, regardless of the above-mentioned weight range.

The form of the transdermal preparation of the present invention is not limited as described above, and the transdermal preparation is preferably a matrix-type transdermal preparation, and more preferably a matrix-type tape preparation. With regard to a form of the matrix-type tape preparation, preferred is one in which a drug-containing layer containing a matrix material, a drug, and the percutaneous absorption enhancer of the present invention is laminated on one surface of a supporting sheet. Here, examples of the matrix material include various adhesive bases. For example, an acrylic adhesive base, a rubber-based adhesive base, a silicone-based adhesive base, or a vinyl ether-based adhesive base each having pressure sensitivity at normal temperature is used as an adhesive base.

Preferred examples of the acrylic adhesive base include a monopolymer having a (meth)acrylic acid alkyl ester (hereinafter, (meth)acrylic acid refers to methacrylic acid or acrylic acid) as a main component, a copolymer of a (meth) acrylic acid alkyl ester and a copolymerizable monomer, or a copolymer of aliphatic alcohol having 4 to 18 carbon atoms and a (meth)acrylic acid alkyl ester.

Examples of the above-mentioned (meth)acrylic acid alkyl ester include (meth)acrylate-2-ethyl hexyl ester, (meth)acrylate ethyl ester, (meth)acrylate butyl ester, (meth)acrylate isobutyl ester, (meth)acrylate hexyl ester, (meth)acrylate octyl ester, (meth)acrylate isooctyl ester, (meth)acrylate decyl ester, (meth)acrylate isodecyl ester, (meth)acrylate lauryl ester, and (meth)acrylate stearyl ester.

Examples of the above-mentioned copolymerizable monomer include acrylic acid, methacrylic acid, maleic acid, maleic anhydride, fumaric acid, crotonic acid, butyl maleate, 2-hydroxyethyl (meth)acrylate, dimethylamino acrylate, hydroxypropyl (meth)acrylate, acrylamide, dimethyl acrylamide, diethyl acrylamide, butoxymethyl acrylamide, ethoxymethyl acrylamide, methylol(meth)acrylamide, N-vinyl-2-pyrolidone, vinyl acetate, vinyl propionate, styrene, α-methylstyrene, vinylchloride, acrylonitrile, ethylene, propylene, and butadiene.

Examples of the rubber-based adhesive base are not particularly limited. There can be used conventionally known rubber-based adhesive base including, as a main component, rubbers such as a natural rubber, polyisoprene, polyisobutylene, polybutadiene, a styrene-butadiene copolymer, a styrene-butadiene-styrene copolymer, a styrene-isoprene copolymer, a styrene-isoprene-styrene copolymer, a styrene-isoprene-styrene block copolymer, a synthetic isoprene rubber, polyvinyl ether, polyurethane, and a urethane rubber.

Examples of the silicone-based adhesive base include, but are not limited to, silicon rubbers such as polyorganosiloxane.

Examples of the vinyl ether-based adhesive base include vinyl ether, isobutyl ether, methyl isobutyl ether, and ethyl isobutyl ether.

In addition, a plasticizer or a tackifier resin can be added to the adhesive base, if required. Examples of the usable plasticizer include petroleum-based oil, squalan, squalene, plant oil, silicone oil, a dibasic acid ester, a liquid rubber, liquid fatty acid esters, diethylene glycol, polyethylene glycol, salicylic acid glycol, propylene glycol, dipropylene glycol, triacetin, triethyl citrate, and crotamiton. Examples of the usable tackifier resin include a rosin derivative, an alicyclic saturated hydrocarbon resin, a terpene resin, and a maleic acid resin.

In addition to the above-mentioned components, there can be used an antioxidant agent, a filler, a cross-linking agent, an antiseptic agent, and a UV absorber. Examples of the antioxidant agent include tocopherol and ester derivatives thereof, ascorbic acid, ascorbyl stearate ester, nordihydroguaiuretic acid, dibutylhydroxytoluene (BHT), and butylhydroxyanisole. Examples of the filler include calcium carbonate, magnesium carbonate, silicate salt, hydrated silica, barium sulfate, calcium sulfate, calcium zincate, zinc oxide, and titanium oxide. Examples of the cross-linking agent include, an amino resin, a phenol resin, an epoxy resin, an alkyd resin, a thermoplastic resin such as an unsaturated polyester, an isocyanate compound, a block isocyanate compound, an organic cross-linking agent, and an inorganic cross-linking agent of metal or a metallic compound. Examples of the antiseptic agent include ethyl parahydroxybenzoate, propyl parahydroxybenzoate, and butyl parahydroxybenzoate. Examples of UV absorber include a p-aminobenzoic acid derivative, an anthranilic acid derivative, a salicylic acid derivative, a coumaric acid derivative, an amino acid compound, an imidazoline derivative, a pyrimidine derivative, and a dioxane derivative.

A tape preparation is obtained, for example, by forming an adhesive layer containing the percutaneous absorption enhancer of the present invention and various drugs on one surface of a support, and then cutting the resultant product into a piece having a predetermined size. Further, the side of the adhesive layer out of contact with the support may be protected with a protector such as a release sheet or protected by forming the tape preparation into a roll form.

The support to be used in the tape preparation of the present invention is preferably one that does not cause reductions in the contents of a sulfosuccinate or a salt thereof, alkyl glycosides, and various drugs each contained in the adhesive layer, the reductions being caused by a phenomenon that some of these substances pass through the support and are lost from the back surface of the support. To be specific, there can be used a woven fabric, a knitted fabric, a non-woven fabric, a film made of any one of, for example, polyvinyl acetate, polyvinylidene chloride, polyethylene, a polyester such as polyethylene terephthalate, nylon, polypropylene, polyvinyl chloride, an ethylene-ethyl acrylate copolymer, polytetrafluoroethylene, cellulose acetate, ethyl cellulose, an ethylene-vinyl acetate copolymer, polyurethane, an ionomer resin, and a metal foil, or a material made by combining these materials. Because the support is required to have flexibility, the thickness of the support is usually 300 μm or less, and preferably 2 to 100 μm or less. Further, the support may also be perforated in order to secure air permeability and moisture permeability to suppress irritation.

The release sheet is necessary to be easily released from the adhesive layer when the release sheet is used. Thus, usually used as the release sheet is, for example, a film made of a polyester such as polyethylene terephthalate, polyvinyl chloride, polyvinylidene chloride, a polyester, or the like, or a laminate film such as glassine paper, the films each having a silicon coat on the surface in contact with the adhesive layer. The thickness of the release sheet is 1000 μm or less, and preferably 30 to 150 μm.

A method of forming an adhesive layer in the tape preparation is not particularly limited, and a solution coating method is preferred. That is, an adhesive base, a drug, a percutaneous absorption enhancer, and various additives, if necessary, are blended, the blend is diluted with and dispersed in an organic solvent to yield a coating liquid, the coating liquid is applied onto a surface of a support with an applicator, and the organic solvent is removed by drying the coating liquid so that an adhesive layer may be formed. Also the above-mentioned coating liquid may be applied onto a release sheet, dried, and then the resultant layer may be transferred to a support. A coating liquid is applied to a release sheet or a support, followed by attachment with a support or a release sheet. Thus the tape preparation of the present invention can be obtained.

EXAMPLES

Hereinafter, the present invention is described in more detail by way of examples. The present invention is not limited to the following examples as long as other examples do not deviate from the gist of the present invention. Note that, in the following respective formulations, the term "%" means the phrase "% by weight (W/W)" unless otherwise specified.

<Permeation Test>

A permeation test was carried out based on the following procedure. First, an excised skin (Yucatan miniature swine or hairless mouse) was placed in a vertical diffusion cell in which temperature was kept at 37° C., and a receptor phase was filled with 7 mL of a phosphate-buffered saline (PBS, a pH of 7.5). The whole was left to stand still for one hour. Then, when a sample was a solution, 1000 μL of the sample solution was added to the stratum corneum side, and when the sample was a tape preparation, a piece obtained by punching out the tape preparation so as to have an area of 1.33 cm$^2$ was attached on the extirpated skin. Then, the test was started. Part of the PBS in the receptor phase was collected every one hour from the start of the test until 8 hours later, and after that, every two hours until 24 hours later. Note that after each of the collections, an equivalent amount of PBS was supplemented into the receptor phase. Each PBS collected from the receptor phase was measured for a drug concentration by an HPLC method. The resultant values were plotted against permeation time, and then the cumulative permeation amount (μg/cm$^2$) of a drug for 24 hours per attachment area of 1 cm$^2$ was calculated. Further, the slant of a permeation curve at the time when the permeation rate reached a steady state was used to calculate a skin permeation rate (μg/hr/cm$^2$).

Example 1

Evaluation of Enhancing Effect on Percutaneous Absorption in Solution System

An enhancing effect on drug permeation was evaluated for the case where a 1% isopropyl myristate solution was used as a control and for the case where 1% each of n-octyl-β-D-thioglucopyranoside and dioctyl sodium sulfosuccinate was added. As the drug, there were used hydralazine hydrochloride, isoxsuprine hydrochloride, phenylephrine hydrochloride, amezinium metilsulfate, urapidil, terazosin hydrochloride, metoprolol tartrate, temocapril hydrochloride, enalapril maleate, cilazapril, trandolapril, lisinopril, perindopril erbumine, imidapril hydrochloride, delapril hydrochloride, ramipril, valsartan, candesartan, olmesartan medoxomil, pitavastatin calcium, fluvastatin sodium, rosuvastatin calcium, atorvastatin calcium, piretanide, furosemide, bumetanide, torasemide, argatroban monohydrate, repaglinide, tazobactam, fexofenadine hydrochloride, methotrexate, cefaclor, levodopa, amoxicillin trihydrate, baclofen, and zanamivir hydrate.

Table 1 shows maximum skin permeation rate and cumulative permeation amount of a drug for 24 hours, obtained in a permeation test using an excised skin of a hairless mouse. As apparent from the comparisons of examples and comparative examples, the percutaneous absorption enhancer of the present invention containing a sulfosuccinate and alkyl glycosides as components remarkably improved the skin permeability of various drugs from respective sample solutions.

TABLE 1

| Drug | Example | | Comparative Example | | Percutaneous absorption enhancing action (Example/Comparative Example) | |
|---|---|---|---|---|---|---|
| | Skin permeation rate (μg/hr/cm$^2$) | Cumulative permeation amount for 24 hours (μg/cm$^2$) | Skin permeation rate (μg/hr/cm$^2$) | Cumulative permeation amount for 24 hours (μg/cm$^2$) | Skin permeation rate (times) | Cumulative permeation amount for 24 hours (times) |
| Hydralazine hydrochloride | 423.2 | 2095.4 | 0.3 | 6.1 | 1,411 | 344 |
| Isoxsuprine hydrochloride | 39.6 | 572.9 | 0.0 | 0.0 | | |
| Phenylephrine hydrochloride | 254.0 | 1750.5 | 32.2 | 475.8 | 8 | 4 |
| Amezinium metilsulfate | 1407.0 | 3270.0 | 58.1 | 502.5 | 24 | 7 |
| Urapidil | 45.8 | 935.4 | 2.6 | 47.0 | 18 | 20 |
| Terazosin hydrochloride | 63.8 | 982.5 | 5.2 | 92.5 | 12 | 11 |
| Metoprolol tartrate | 137.1 | 1792.8 | 29.6 | 422.9 | 5 | 4 |
| Temocapril hydrochloride | 461.7 | 5107.5 | 10.1 | 192.5 | 46 | 27 |
| Enalapril maleate | 1009.7 | 5127.5 | 22.9 | 1332.5 | 44 | 4 |
| Cilazapril | 265.3 | 3690.0 | 17.0 | 280.0 | 16 | 13 |
| Trandolapril | 386.8 | 4627.5 | 7.2 | 375.0 | 54 | 12 |
| Lisinopril | 259.3 | 23190.0 | 26.9 | 527.5 | 10 | 44 |
| Perindopril erbumine | 1063.1 | 5352.5 | 88.2 | 1605.0 | 12 | 3 |
| Imidapril hydrochloride | 693.6 | 4017.5 | 17.2 | 332.5 | 40 | 12 |
| Delapril hydrochloride | 49.5 | 1045.0 | 1.9 | 25.0 | 26 | 42 |
| Ramipril | 576.9 | 6655.0 | 71.2 | 1422.5 | 8 | 5 |
| Valsartan | 551.2 | 6462.5 | 45.5 | 1567.5 | 12 | 4 |
| Candesartan | 109.6 | 71.9 | 0.6 | 4.7 | 183 | 15 |
| Olmesartan medoxomil | 41.5 | 836.7 | 0.44 | 11.2 | 94 | 75 |
| Fluvastatin sodium | 27.2 | 1130.0 | 0.5 | 40.0 | 54 | 28 |
| Rosuvastatin calcium | 385.5 | 3682.5 | 2.8 | 80.0 | 138 | 46 |
| Atorvastatin calcium | 19.6 | 437.5 | 0.2 | 2.2 | 98 | 199 |

TABLE 1-continued

|  | Example | | Comparative Example | | Percutaneous absorption enhancing action (Example/Comparative Example) | |
|---|---|---|---|---|---|---|
| Drug | Skin permeation rate ($\mu$g/hr/cm$^2$) | Cumulative permeation amount for 24 hours ($\mu$g/cm$^2$) | Skin permeation rate ($\mu$g/hr/cm$^2$) | Cumulative permeation amount for 24 hours ($\mu$g/cm$^2$) | Skin permeation rate (times) | Cumulative permeation amount for 24 hours (times) |
| Piretanide | 187.9 | 3517.5 | 3.7 | 105.0 | 51 | 34 |
| Furosemide | 318.9 | 5125.0 | 7.1 | 167.5 | 45 | 31 |
| Bumetanide | 198.3 | 3320.0 | 4.0 | 1107.5 | 50 | 3 |
| Torasemide | 59.7 | 1150.0 | 1.5 | 40.0 | 40 | 29 |
| Argatroban monohydrate | 121.3 | 2270.0 | 0.9 | 23.0 | 135 | 99 |
| Repaglinide | 26.0 | 607.5 | 0.8 | 22.3 | 33 | 27 |
| Tazobactam | 610.9 | 3710.0 | 28.8 | 670.0 | 21 | 6 |
| Fexofenadine hydrochloride | 74.3 | 1252.5 | 1.7 | 22.5 | 44 | 56 |
| Methotrexate | 53.9 | 1497.5 | 0.3 | 6.0 | 180 | 250 |
| Cefaclor | 288.7 | 1385.0 | 0.3 | 3.3 | 962 | 420 |
| Levodopa | 433.4 | 6817.5 | 1.5 | 14.8 | 289 | 461 |
| Amoxicillin trihydrate | 254.0 | 3930.0 | 1.0 | 16.8 | 254 | 234 |
| Baclofen | 238.3 | 5477.5 | 0.0 | 0.0 | | |
| Zanamivir hydrate | 654.4 | 6015.1 | 7.1 | 128.4 | 92 | 47 |

The tape preparations of Examples 2 to 14 and Comparative Examples 2 to 10 were obtained by the following production method in accordance with each of the formulations shown in Tables 2 to 6.

An organic solvent such as methanol, acetone, dichloromethane, toluene, or hexane was appropriately added to constituent components, and the whole was stirred so as to result in a uniform solution. The resultant coating liquid was applied onto a support made of polyethylene terephthalate and subjected to a corona discharge treatment. After the solution was removed by drying, a release sheet made of polyethylene terephthalate and subjected to a Teflon (registered trademark) coating treatment was attached to the support, thereby yielding a tape preparation of the present invention. Bumetanide as a loop-based diuretic drug, brotizolam, estazolam, flunitrazepam and triazolam as benzodiazepine hypnotics, and temocapril hydrochloride, enalapril maleate and cilazapril as angiotensin-converting enzyme inhibitors were used as drug serving.

TABLE 2

| Component | Example 2 | Example 3 | Example 4 | Comparative Example 2 | Comparative Example 3 | Comparative Example 4 |
|---|---|---|---|---|---|---|
| Bumetanide | 10% | 10% | 10% | 10% | 10% | 5% |
| n-octyl-$\beta$-D-thioglucopyranoside | 2.5% | 2.5% | — | 2.5% | — | — |
| n-dodecyl-$\beta$-D-glucopyranoside | — | — | 2.5% | — | — | 5% |
| Dioctyl sodium sulfosuccinate | 5% | 5% | 5% | — | 5% | — |
| Diethyl sebacate | — | — | — | — | — | 5% |
| Aluminum acetylacetonate | — | — | — | — | — | 1% |
| Isopropyl myristate | 30% | 27.5% | 27.5% | 30% | 30% | 30% |
| GELVA (Registered trademark, Cytech, Inc.) Multipolymer Solution 1430 | 52.5% | 55% | 55% | 57.5% | 55% | — |
| Duro-Tak (Registered trademark, National Starch and Chemical Company) 387-2516 | — | — | — | — | — | 54% |

TABLE 3

| Component | Example 5 | Example 6 | Example 7 | Comparative Example 5 |
|---|---|---|---|---|
| Brotizolam | 2.5% | 2.5% | 2.5% | 5% |
| n-dodecyl-$\beta$-D-glucopyranoside | 5% | 5% | 5% | — |
| Dioctyl sodium sulfosuccinate | 5% | 5% | 5% | — |
| Isopropyl myristate | 30% | 30% | 30% | 40% |
| Duro-Tak (Registered trademark) 387-2516 | 57.5% | — | — | 55% |
| Quintac (Registered trademark, Zeon Corporation) 3570C (Styrene-isoprene block polymer) | — | 28.8% | — | — |

TABLE 3-continued

| Component | Example 5 | Example 6 | Example 7 | Comparative Example 5 |
|---|---|---|---|---|
| Arkon (Registered trademark, Arakawa Chemical Industries, Ltd.) M-135 (Alicyclic petroleum resin) | — | 28.8% | 23% | — |
| Oppanol (Registered trademark, BASF) B150 (High-molecular-weight polyisobutylene) | — | — | 11.5% | — |
| Himol 4H (Nippon Oil Corporation, Low-molecular-weight polyisobutylene) | — | — | 23% | — |

TABLE 4

| Component | Example 8 | Example 9 | Example 10 | Example 11 | Example 12 |
|---|---|---|---|---|---|
| Estazolam | 5.0% | — | — | — | — |
| Flunitrazepam | — | 5.0% | — | — | — |
| Triazolam | — | — | 5.0% | — | — |
| Temocapril hydrochloride | — | — | — | 2.0% | — |
| Enalapril maleate | — | — | — | — | 3.0% |
| n-octyl-β-D-thioglucopyranoside | 1.0% | 1.0% | 1.0% | 0.5% | 0.5% |
| Dioctyl sodium sulfosuccinate | 1.0% | 1.0% | 1.0% | 1.0% | 1.0% |
| YS Polystar T100 (Yasuhara Chemical Co., Ltd., Tackifier resin) | 9.0% | 9.0% | 9.0% | — | — |
| Isopropyl myristate | 29.0% | 29.0% | 29.0% | 30.0% | 30.0% |
| Duro-Tak (Registered trademark) 87-2852 | 55.0% | 55.0% | 55.0% | — | — |
| GELVA (Registered trademark) Multipolymer Solution 2999 | — | — | — | 66.5% | 65.5% |

TABLE 5

| Component | Example 13 | Comparative Example 6 | Comparative Example 7 | Comparative Example 8 |
|---|---|---|---|---|
| Cilazapril | 3.0% | 3.0% | 3.0% | 3.0% |
| n-octyl-β-D-thioglucopyranoside | 0.5% | 0.5% | — | — |
| Dioctyl sodium sulfosuccinate | 1.0% | — | 1.0% | — |
| Isopropyl myristate | 50.0% | 50.0% | 50.0% | 50.0% |
| GELVA (Registered trademark) Multipolymer Solution 1753 | 45.5% | 46.5% | 46.0% | 47.0% |

TABLE 6

| Component | Example 14 | Comparative Example 9 | Comparative Example 10 |
|---|---|---|---|
| Bumetanide | 5% | 5% | 5% |
| n-octyl-β-D-thioglucopyranoside | 2.5% | 2.5% | — |
| Dioctyl sodium sulfosuccinate | 5% | — | 5% |
| Isopropyl myristate | 30% | 30% | 30% |
| GELVA (Registered trademark) Multipolymer Solution 1430 | 57.5% | 62.5% | 60% |

Test Example 1

In Vitro Permeation Test Using Excised Skin of Yucatan Miniature Swine

A permeation test was carried out on each of the preparations obtained in Example 2, and Comparative Examples 2 and 3 by using an excised skin of a Yucatan miniature swine. Further, after the completion of the test, each preparation was collected to measure the content of the drug in the preparation. The difference between the content of the drug before the start of the test and that after the completion of the test was used to calculate the drug release amount from the preparation. Here, the content of the drug was determined by extracting the drug in the preparation with 10 mL of methanol and measuring a drug concentration by an HPLC method. As evident from the results shown in Table 7, the tape preparation (Example 2) containing the percutaneous absorption enhancer of the present invention, the enhancer containing a sulfosuccinate or a salt thereof and alkyl glycosides as components, released a similar amount of a drug to the amounts of Comparative Examples 2 and 3. On the other hand, the tape preparation (Example 2) exhibited a high skin permeation rate of a drug and effectively permeated the drug released from the preparation into the skin, compared with Comparative Examples 2 and 3.

TABLE 7

| Permeation parameter | Example 2 | Comparative Example 2 | Comparative Example 3 |
|---|---|---|---|
| Skin permeation rate ($\mu g/hr/cm^2$) | 2.33 | 1.28 | 0.89 |
| Cumulative permeation amount for 24 hours ($\mu g$) | 36.0 | 21.1 | 13.1 |
| Drug release amount from preparation ($\mu g$) | 54.4 | 54.9 | 54.3 |
| Cumulative permeation amount for 24 hours/Drug release amount from preparation | 0.662 | 0.384 | 0.241 |

Test Example 2

Comparison of Permeability of Tape Preparations Using Various Adhesive Bases (1) A permeation test was carried out on each of the tape preparations of Examples 5 to 7 and Comparative Example 5 by using an excised skin of a male hairless mouse. As evident from the results shown in Table 8, the tape preparations (Examples 5 to 7) each containing the percutaneous absorption enhancer of the present invention, the enhancer containing a sulfosuccinate or a salt thereof and alkyl glycosides as components, exhibited a high skin permeation rate of a drug and exhibited a remarkable increase in the cumulative permeation amount for 24 hours, compared with the tape preparation (Comparative Example 5) free of the enhancer of the present invention.

An acrylic adhesive base was used in Example 5 and a rubber-based adhesive base was used in each of Examples 6 and 7. The percutaneous absorption enhancer of the present invention containing a sulfosuccinate or a salt thereof and alkyl glycosides as components exerted its effects even if any one of these adhesive bases was used, and the enhancer did not prevent the adhesiveness of the adhesive bases. The results described above clarified that the percutaneous absorption enhancer of the present invention was one which was excellent in compatibility with various adhesive bases usually used in tape preparations.

TABLE 8

| Permeation parameter | Example 5 | Example 6 | Example 7 | Comparative Example 5 |
|---|---|---|---|---|
| Skin permeation rate ($\mu g/hr/cm^2$) | 3.2 | 10.9 | 4.1 | 0.69 |
| Cumulative permeation amount for 24 hours ($\mu g/cm^2$) | 72.8 | 243.1 | 101.5 | 12.9 |

(2) A permeation test was carried out on each of the tape preparations of Example 13 and Comparative Examples 6 to 8 by using an excised skin of a male hairless mouse. As evident from the results shown in Table 9, the tape preparations (Example 13) containing the percutaneous absorption enhancer of the present invention, the enhancer containing a sulfosuccinate or a salt thereof and alkyl glycosides as components, exhibited a high skin permeation rate of a drug and exhibited a remarkable increase in the cumulative permeation amount for 24 hours, compared with the tape preparations (Comparative Examples 6 to 8) free of the enhancer of the present invention.

TABLE 9

| Permeation parameter | Example 13 | Comparative Example 6 | Comparative Example 7 | Comparative Example 8 |
|---|---|---|---|---|
| Skin permeation rate ($\mu g/hr/cm^2$) | 27.4 | 2.47 | 7.76 | 1.22 |
| Cumulative permeation amount for 24 hours ($\mu g/cm^2$) | 271.0 | 86.2 | 229.4 | 55.3 |

Test Example 3

Measurement of Concentration in Blood Plasma Using Rat

Each of the tape preparations of Examples 3, 4, and 14, and Comparative Examples 4, 9, and 10 was attached on the back of a hairless rat for 24 hours, and time-dependent blood collection was carried out. A liquid chromatograph mass spectrometer was used to measure a bumetanide concentration in the blood plasma of the rat.

As evident from Tables 10 and 11, the tape preparations (Examples 3, 4, and 14) each containing the percutaneous absorption enhancer of the present invention, the enhancer containing a sulfosuccinate or a salt thereof and alkyl glycosides as components, were preparations excellent in the skin permeability of a drug and drug transitivity into the body, compared with Comparative Examples 4, 9, and 10 which include different combinations of enhancers.

TABLE 10

| | Measurement of concentration in rat blood plasma | | |
|---|---|---|---|
| | Cmax (ng/mL) | Tmax (hr) | AUC (ng · hr/mL) |
| Example 3 | 119 | 20.0 | 1713 |
| Example 4 | 117 | 20.0 | 1689 |
| Comparative Example 4 | 7.1 | 14.0 | 115.8 |

TABLE 11

| | Measurement of concentration in rat blood plasma | | |
|---|---|---|---|
| | Cmax (ng/mL) | Tmax (hr) | AUC (ng · hr/mL) |
| Example 14 | 89.6 | 20.0 | 1283 |
| Comparative Example 9 | 19.9 | 16.0 | 302.3 |
| Comparative Example 10 | 41.2 | 20.0 | 541.3 |

Test Example 4

Confirmation of Pharmacological Effect and Measurement of Concentration in Blood Plasma Using Dog Each of the tape preparations of Examples 3 and 4 was cut into a piece having an area of 80 cm², and the resultant piece was attached on the sheared thoracoabdominal part of a beagle dog for 48 hours. When 48 hours elapsed after the administration, the preparation was detached, and then the amount of urine was measured until 72 hours after the administration. Further, time-dependent blood collection was carried out, and a liquid chromatograph mass spectrometer was used to measure a bumetanide concentration in the blood plasma of the dog.

Table 12 shows each ratio of the amount of urine for 24 hours with respect to a control. In the change of the amount of urine for every 24 hours, a peak of the action of increasing the amount of urine was found at 24 hours after the attachment in a group of dogs on which the tape preparation of Example 3 had been attached, and was found at 48 hours after the attachment in a group of dogs on which the tape preparation of Example 4 had been attached. Further, an increase in a bumetanide concentration in blood plasma was found at an early stage after the attachment in the group of dogs on which the tape preparation of Example 3 had been attached, compared with the group of dogs on which the tape preparation of Example 4 had been attached. The result was in agreement with the ratio of the increase in the amount of urine for 24 hours with respect to the control.

The results described above clarified that n-octyl-β-D-thioglucopyranoside used in Example 3 was more preferred in terms of skin permeability in large animals out of alkyl glycosides.

TABLE 12

| | Ratio (%) of amount of urine for 24 hours with respect to control | | |
|---|---|---|---|
| | 0 to 24 hours after administration | 24 to 48 hours after administration | 48 to 72 hours after administration |
| Example 3 | 202.5 | 148.3 | 111.9 |
| Example 4 | 132.3 | 197.6 | 134.4 |

Test Example 5

Primary Skin Irritation Test on Rabbit

Draize Method

The back of each Japanese White rabbit (male, having a weight of about 2 kg) was carefully sheared with an electric shaver one day before the test. A piece obtained by cutting each of the tape preparations (Examples 15 to 20) so as to have a round shape with a diameter of 2.5 cm (4.91 cm$^2$) was attached on the back for 24 hours. 24 hours later, the tape preparation was removed. Immediately after the tape preparation was detached and when 48 hours elapsed after the detachment, skin conditions were determined based on the following scores of the Draize method. The scores of the respective skin conditions were used to determine Primary Skin Irritation Index (P. I. I.). Table 13 shows the formulations and results of Examples 15 to 20. Note that each preparation was produced in the same manner as that in Example 2.

<Grading Criteria Based on Draize Method>

Erythema and Eschar Formation

0: No erythema

1: Very slight erythema (barely perceptible)

2: Well-defined erythema

3: Moderate to severe erythema

4: Severe erythema to slight eschar (injuries in depth) formation

Edema Formation

0: No edema

1: Very slight edema (barely perceptible)

2: Slight edema (edge of area well defined by definite raising)

3: Moderate edema (raised approximately 1 mm)

4: Severe edema (raised more than 1 mm and extending beyond area of exposure)

<Calculation Method of Scores of Draize Method>

Immediately after each tape preparation was detached and when 48 hours elapsed after the detachment, the tape preparation was graded for two evaluation items, erythema and eschar formation and edema formation, based on the above-mentioned grading criteria of the Draize method. Scores for the erythema and eschar formation and scores for the edema formation for respective grading times were summed and the resultant total values were divided by the number of rabbits, thereby calculating average values for respective grading times. The average values were defined as Primary Skin Irritation Index (P. I. I.).

<Safety Classification of Draize Method>

Safety Classification Primary Skin Irritation Index (P. I. I.)

| Mild irritant | P.I.I. ≤ 2 |
|---|---|
| Moderate irritant | 2 < P.I.I. ≤ 5 |
| Strong irritant | 5 < P.I.I. |

TABLE 13

| Component | Example 15 | Example 16 | Example 17 | Example 18 | Example 19 | Example 20 |
|---|---|---|---|---|---|---|
| Bumetanide | 2.5% | 2.5% | 2.5% | 2.5% | 2.5% | 2.5% |
| n-octyl-β-D-thioglucopyranoside | 1% | 1% | 1% | 2.5% | 2.5% | 2.5% |
| Dioctyl sodium sulfosuccinate | 1% | 2.5% | 5% | 1% | 2.5% | 5% |
| Isopropyl myristate | 30% | 30% | 30% | 30% | 30% | 30% |
| GELVA (Registered trademark) Multipolymer Solution 1430 | 65.5% | 64% | 61.5% | 64% | 62.5% | 60% |
| P.I.I. | 1.3 | 1.8 | 2.0 | 0.5 | 0.5 | 1.3 |

The tape preparations obtained in accordance with the formulations shown in Examples 15 to 20 were classified into the category of "mild irritant" based on the above-mentioned safety classification of the Draize method. Thus, those tape preparations were determined to have weak primary skin irritation.

Note that P. I. I. is a value including a value representing the skin irritation of a drug itself. Thus, those results do not restrict the blending amounts of a sulfosuccinate or a salt thereof and alkyl glycosides in the present invention.

Test Example 6

Skin Sensitization Test Using Guinea Pig

Adjuvant and Patch Test Method

A skin sensitization test was carried out on a tape preparation being free of a drug and containing the percutaneous absorption enhancer of the present invention, the enhancer containing dioctyl sodium sulfosuccinate and n-octyl-β-D-thioglucopyranoside as components, by the Adjuvant and Patch test method using a guinea pig. As a result, the finding that the expression of skin sensitization might have occurred was not observed.

Test Example 7

Adhesive Force Test

Tape preparations were produced in accordance with the formulations in Table 14 in the same manner as that in Example 2.

TABLE 14

| Component | Example 21 | Comparative Example 11 |
|---|---|---|
| Bumetanide | 5% | 5% |
| n-dodecyl-β-D-glucopyranoside | 2.5% | 2.5% |
| Dioctyl sodium sulfosuccinate | 5% | — |
| Isopropyl myristate | 30% | 30% |
| Duro-Tak (Registered trademark) 387-2516 | 57.5% | 62.5% |

Each of the preparations obtained in Example 21 and Comparative Example 11 was cut into a piece of 12 mm wide by 70 mm long. Thin paper was attached on a part of about 15 mm long of the piece as a guide, and the resultant piece was used as a test piece. The test piece was attached to a test plate made of Bakelite. Immediately after that, a rubber roller having a weight of 850 g was passed twice on the test piece at a speed of 300 mm/min. The test plate with the test piece was left to stand still for 30 minutes in an atmosphere of a temperature of 23° C.±2° C. and was then set in a tensile tester. The guide of the test piece was folded by 180° to peel the test piece by about 5 mm long. After that, the test piece was sequentially peeled at a speed of 300 mm/min, thereby measuring its adhesive force. As the results in Table 15 show, the tape preparation of the present invention had a favorable adhesive force, while the tape preparation of Comparative Example 11 including only alkyl glycosides had a very low adhesive force.

TABLE 15

| | Example 21 | Comparative Example 11 |
|---|---|---|
| adhesive force (N/12 mm) | 2.84 | 0.366 |

The invention claimed is:

1. A matrix-type transdermal preparation, comprising:
a tape comprising drug containing layers comprising an adhesive base,
a percutaneous absorption enhancer comprising 0.01 to 10% of a sulfosuccinate or a salt thereof and 0.01 to 10% of an alkyl glycoside or an alkyl thioglycoside, wherein the sulfosuccinate or a salt thereof and the alkyl glycoside or the alkyl thioglycoside are present in a total amount of from 0.1 to 20%; and
a drug.

2. The matrix-type transdermal preparation according to claim 1, wherein the sulfosuccinate or the salt thereof is a $C_6$-$C_{18}$ dialkyl sulfosuccinate or a salt thereof.

3. The matrix-type transdermal preparation according to claim 1, wherein the alkyl glycoside or the alkyl thioglycoside is a $C_6$-$C_{18}$ alkyl glycoside or a $C_6$-$C_{18}$ alkyl thioglycoside.

4. The matrix-type transdermal preparation according to claim 1, wherein the sulfosuccinate or the salt thereof is a dioctyl sulfosuccinate or a salt of the dioctyl sulfosuccinate.

5. The matrix-type transdermal preparation according to claim 1, wherein the alkyl glycoside or the alkyl thioglycoside is an n-octyl-β-D-thioglucopyranoside or an n-dodecyl-β-D-glucopyranoside.

6. The matrix-type transdermal preparation according to claim 1, wherein each of the drug containing layers comprises an adhesive base, the drug, and the percutaneous absorption enhancer laminated on one surface of a supporting sheet.

7. The matrix-type transdermal preparation according to claim 6, wherein the adhesive base consists of an acrylic adhesive base, a rubber-based adhesive base, or a silicone-based adhesive base.

8. The matrix-type transdermal preparation according to claim 1, wherein the drug is a compound having a carboxyl group or a bioisoster thereof and an aliphatic amino group and/or an aromatic amino group.

9. A method of enhancing percutaneous absorption of a drug, the method comprising transdermally administering a matrix-type transdermal tape preparation comprising the drug with a percutaneous absorption enhancer comprising 0.01 to 10% of a sulfosuccinate or a salt thereof, and 0.01 to 10% of an alkyl glycoside or an alkyl thioglycoside, wherein the sulfosuccinate or a salt thereof and the alkyl glycoside or the alkyl thioglycoside are present in a total amount of from 0.1 to 20%.

10. The method according to claim 9, wherein the drug and the sulfosuccinate or a salt thereof, and an alkyl glycoside or an alkyl thioglycoside are in the matrix-type transdermal tape preparation.

11. The method according to claim 9, wherein the matrix type transdermal tape preparation comprises drug-containing layers, wherein each of the drug containing layers comprises an adhesive base, the drug, and the percutaneous absorption enhancer laminated on one surface of a supporting sheet.

12. The method according to claim 11, wherein the adhesive base consists of an acrylic adhesive base, a rubber-based adhesive base, or a silicone-based adhesive base.

13. The method according to claim 9, wherein the drug is a compound having a carboxyl group or a bioisoster thereof and an aliphatic amino group and/or an aromatic amino group.

14. The matrix-type transdermal preparation according to claim 1, wherein the adhesive base is alkyl acrylate adhesive.

* * * * *